US011596831B2

(12) United States Patent
Johnson et al.

(10) Patent No.: US 11,596,831 B2
(45) Date of Patent: Mar. 7, 2023

(54) SYSTEM AND METHOD FOR PROVIDING INDIRECT MOVEMENT FEEDBACK DURING SENSORIMOTOR FUNCTION REHABILITATION AND ENHANCEMENT

(71) Applicant: IREGAINED INC., Sudbury (CA)

(72) Inventors: Vineet Benjamin K. Johnson, Sudbury (CA); Ranjit Solomon Stanley, Indianapolis, IN (US); Daniel Vasiliu, Thunder Bay (CA)

(73) Assignee: IREGAINED INC., Sudbury (CA)

( * ) Notice: Subject to any disclaimer, the term of this patent is extended or adjusted under 35 U.S.C. 154(b) by 373 days.

(21) Appl. No.: 16/756,640

(22) PCT Filed: Oct. 18, 2018

(86) PCT No.: PCT/CA2018/051313
§ 371 (c)(1),
(2) Date: Apr. 16, 2020

(87) PCT Pub. No.: WO2019/075567
PCT Pub. Date: Apr. 25, 2019

(65) Prior Publication Data
US 2020/0254305 A1 Aug. 13, 2020

Related U.S. Application Data

(60) Provisional application No. 62/573,879, filed on Oct. 18, 2017.

(51) Int. Cl.
*A63B 23/16* (2006.01)
*A61B 5/11* (2006.01)
(Continued)

(52) U.S. Cl.
CPC ............ *A63B 23/16* (2013.01); *A61B 5/1125* (2013.01); *A61B 5/486* (2013.01);
(Continued)

(58) Field of Classification Search
CPC . A63B 23/16; A63B 21/0442; A63B 24/0062; A63B 2071/065; A63B 2209/00;
(Continued)

(56) References Cited

U.S. PATENT DOCUMENTS 3,782,719 A * 1/1974 Kuhlman ............... A63B 23/16
84/467
4,875,469 A * 10/1989 Brook .................. A61H 1/0288
601/40
(Continued)

FOREIGN PATENT DOCUMENTS

CN 204428386 U 7/2015
CN 105999652 A 10/2016
(Continued)

OTHER PUBLICATIONS

International Search Report of the parent PCT application PCT/CA2018/051313 filed Oct. 18, 2018, dated Feb. 7, 2019.

*Primary Examiner* — Joshua Lee
*Assistant Examiner* — Catrina A Letterman
(74) *Attorney, Agent, or Firm* — Hill & Schmacher

(57) ABSTRACT

A rehabilitation feedback system is used during rehabilitation of one or more body appendages of a user. The system includes four finger tracking elements and a thumb tracking element supported for movement relative to one another so as to allow a user to performs a gripping motion when the elements are coupled to the fingers and thumb of a user. A biasing member provides a resistance force acting to urge each tracking element towards a starting position thereof. A visual barrier is adapted to hide the hand of the user at a first side of the visual barrier from direct visual sight by the user at a second side of the visual barrier. A sensor at the first side of the visual barrier detects movements of the tracking elements and communicates with an indicator element (Continued)

detectable by the user from a second side of the visual barrier.

20 Claims, 6 Drawing Sheets

(51) Int. Cl.
    *A61B 5/00*     (2006.01)
    *A63B 21/04*     (2006.01)
    *A63B 24/00*     (2006.01)
    *A63B 71/06*     (2006.01)

(52) U.S. Cl.
    CPC ...... *A63B 21/0442* (2013.01); *A63B 24/0062* (2013.01); *A63B 2071/065* (2013.01); *A63B 2209/00* (2013.01)

(58) Field of Classification Search
CPC . A63B 21/0552; A63B 71/06; A63B 71/0619; A63B 2071/0625; A63B 2220/51; A63B 2220/80; A63B 2220/89; A63B 2225/20; A63B 21/00058; A63B 21/00069; A63B 21/00072; A63B 21/02; A63B 21/026; A63B 21/04; A63B 21/4001; A63B 21/4019; A63B 2213/00; A63B 2220/83; A63B 2220/833; A61B 5/1125; A61B 5/486; A61B 2505/09; A61B 5/225; A61B 5/11; A61B 5/1124; A61B 5/1126; A61H 2201/1261; A61H 2201/1635; A61H 2201/5043; A61H 2201/5061; A61H 2230/00; A61H 1/0285; A61H 1/0288; A61H 2201/1253–1276; A61H 2201/5064; A61H 2205/067
USPC .................................................. 600/587, 595
See application file for complete search history.

(56) References Cited

U.S. PATENT DOCUMENTS

| | | | |
|---|---|---|---|
| 5,451,191 A * | 9/1995 | Beenken | A63B 23/16 |
| | | | 601/40 |
| 5,697,103 A | 12/1997 | Wiggins | |
| 11,141,341 B2 * | 10/2021 | Koltzi | A63B 22/00 |
| 2002/0146672 A1 * | 10/2002 | Burdea | A63B 23/16 |
| | | | 434/258 |
| 2007/0072752 A1 | 3/2007 | Koch et al. | |
| 2010/0311546 A1 * | 12/2010 | Kupferman | A63B 21/4025 |
| | | | 482/47 |
| 2011/0071443 A1 * | 3/2011 | Weisz | A61H 1/0237 |
| | | | 601/40 |
| 2016/0144228 A1 | 5/2016 | Jung | |
| 2017/0099468 A1 * | 4/2017 | Tanaka | H04N 9/3194 |
| 2020/0215329 A1 * | 7/2020 | Kilgard | A61N 1/37211 |

FOREIGN PATENT DOCUMENTS

| | | | | |
|---|---|---|---|---|
| CN | 107158660 | * | 9/2017 | .......... A61H 1/0288 |
| CN | 107158660 A | | 9/2017 | |
| TW | 200724125 A | | 7/2007 | |
| WO | 2005074371 A2 | | 8/2005 | |
| WO | 2005074371 A3 | | 8/2005 | |
| WO | 2016020457 A1 | | 2/2016 | |
| WO | 2016149652 A1 | | 9/2016 | |

* cited by examiner

SYSTEM AND METHOD FOR PROVIDING INDIRECT MOVEMENT FEEDBACK DURING SENSORIMOTOR FUNCTION REHABILITATION AND ENHANCEMENT

FIELD OF THE INVENTION

The present invention relates to a system and a method of use of the system to provide resistance to a movement of an appendage of a user during rehabilitation of control of that appendage and to provide feedback to the user relating to the movement in an indirect manner so that the appendage is not directly visible to the user.

BACKGROUND

The term "sensorimotor function" refers to the ability of a human to gather sensorial information (tactile, proprioceptive) and use such information to generate motor commands for the skeletal muscles, voluntary and involuntary. The sensorimotor function uses the nervous system to feed sensorial information from the periphery (tactile info, joint angles through proprioception) to the brain via sensory neurons, process it in the central nervous system (brain, spinal cord) and send motor commands to the skeletal muscles, via motor neurons, to move the bones about their joints. The proper functionality of the sensory cells, nerves and muscles is essential to performing any kind of physical activity (walking, working, activities of daily living).

Conditions like stroke or bodily injury cause damage to one or more of the elements involved in the sensorimotor function performance. This damage manifests itself as functional impairments ranging from slight losses of precision and power, to total inability to move a limb or part thereof, combined with no sensorial (tactile, proprioceptive) information.

At the other end of the spectrum, healthy individuals may want to train their sensorimotor function to increase their performance above the average. Typical cases include, but are not limited to workers assembling miniature electronic devices such as smartphones, neurosurgeons for whom eye-hand coordination is critical, fighter jet pilots training their precise manual control of the aircraft in flight, otherwise healthy elderly population.

There currently exist two types of devices designed for this field: passive (gloves, braces, exo-skeletal structures) and active (electronic muscle stimulators, robotic devices, exo-skeletal or endo-skeletal structures).

Passive devices—such as spring-loaded gloves and exo-skeletal frames—limit the limb range of motion or facilitate movements around joints by compensating for spasticity. Spasticity is a condition characterized by a strong, involuntary contraction of one muscle or muscle group, blocking the antagonist (counter-acting) muscle or muscle group and making voluntary movements around the joint painful and/or very difficult/impossible. These devices are designed to partially compensate for the underperformance of one or more components of the sensorimotor system.

A typical example is the Therapeutic Glove (U.S. Pat. No. 5,697,103 A) which describes a glove made of rigid segments joined at the finger joints level and having a system of springs on the outer side that extend the hand of the person wearing it, thus compensating for the tendency of the impaired hand to close in a deformed, spastic fist.

Active devices, such as robotic systems or electronic muscle stimulators, work by moving the limb on behalf of the patient through external electrical stimulation of the muscles, or by actively aiding or resisting, to various extents, the movement through external actuators.

Their function can be controlled via software, via patient voice control or by direct interfacing with the patient's nervous system through skin contacts.

Such devices are either custom-made, as part of clinical or academic research programs, or commercially available. In both cases they are very complex and prohibitively expensive ($100,000+). They must be operated by qualified personnel in a tightly controlled environment (clinical or academic), and are usually out of reach for the vast majority of potential users.

There currently exists no proven method to provide affordable and effective rehabilitation to stroke survivors. The existing passive methods assist range of motion (alleviate a symptom) without improving the core problem of impaired sensorimotor functionality of the hand. The existing active devices, while interacting with the patient's sensorimotor system, are not designed for mass-market applications, impossible to use on a large scale (either privately in-home or at community-level) and prohibitively expensive.

SUMMARY OF THE INVENTION

The system and method according to the present invention addresses functional needs in the healthcare and wellbeing field, such as the field of rehabilitation of patients with motor skill impairments of various types, for example post-stroke impairments or traumatic brain injuries of the type which may be present in war veterans or athletes and the like, or development of precise motor skills in healthy individuals. According to one aspect of the invention there is provided a rehabilitation feedback system for use during rehabilitation of control by a user of one or more body appendages of the user, the system comprising:

a base frame;

at least one working element supported on the base frame so as to be movable relative to the base frame from a starting position to a deflected position, said at least one working element being adapted to be coupled to a respective one of the one or more body appendages of the user for movement with the body appendage relative to the base frame;

a biasing member operatively connected between the base frame and said at least one working element so as to provide a resistance force acting to urge said at least one working element towards the starting position;

a visual barrier adapted to hide the one or more body appendages of the user at a first side of the visual barrier from direct visual sight by the user at a second side of the visual barrier;

a sensor element at the first side of the visual barrier so as to be arranged to detect movement of said at least one working element away from the starting position; and an indicator element which is detectable by the user from a second side of the visual barrier and which is arranged to indicate to the user a displacement of said at least one working element in response to detection by the sensor element that said at least one working element has moved away from the starting position.

According to a second aspect of the present invention the rehabilitation feedback system described above is used to provide feedback to a user relating to a movement of one or more body appendages of the user during rehabilitation of control by the user of the one of more body appendages.

According to a further aspect of the present invention there is provided a method of providing movement feedback to a user undergoing rehabilitation of control by the user of a body appendage of the user, the method comprising:

providing a rehabilitation feedback system comprising (i) a base frame, (ii) at least one working element supported on the base frame so as to be movable relative to the base frame from a starting position to a deflected position, (iii) a biasing member operatively connected between the base frame and said at least one working element so as to provide a resistance force acting to urge said at least one working element towards the starting position, (iv) a sensor element arranged to detect movement of said at least one working element away from the starting position, and (v) an indicator element arranged to indicate to the user a displacement of said at least one working element in response to detection by the sensor element that said at least one working element has moved away from the starting position;

providing a visual barrier in proximity to the rehabilitation system such that said at least one working element is hidden at a first side of the visual barrier from direct visual sight by the user at a second side of the visual barrier;

locating the indicator element so as to be detectable by a user from the second side of the visual barrier; and operating the feedback mechanism such that any movement relative to the base frame of a body appendage of the user that is coupled to said at least one working element at the first side of the visual barrier is indicated to the user in a manner that is detectable by the user from the second side of the visual barrier.

Unlike existing implementations, the present invention works by addressing the underlying cause of the impairments (or improve functional performance in healthy individuals). It does this via a hardware implementation that is simple, easy to use and easy to manufacture on a large scale. The present invention can be implemented as very basic, affordable units, or as more sophisticated products (capable of remote access, team workouts and online championships, self-learning, artificial intelligence) to match the preferences and requirements of a wide base of potential users worldwide.

The device for sensorimotor function rehabilitation and enhancement, as described herein preferably comprises a device that attaches to the extremities (distal phalanges) of the fingers of one hand in order to offer individually adjustable and arbitrarily programmable resistance and range of motion for each finger. The device prevents the user from seeing their exercising hand while using the device, instead providing indirect performance feedback via a separate user interface. The device enhances neuroplasticity through indirect performance feedback to restore and enhance the sensorimotor function. The device preferably provides multi-axial positioning to accommodate functional abilities/differences of upper extremities. Preferably, the device also provides adjustable spacing and attachment for fingers, to accommodate various hand and finger sizes.

In the illustrated embodiment, said at least one working element comprises a plurality of finger tracking elements arranged to be coupled to respective fingers of the user for tracking a gripping motion of the fingers of the user. In this instance, the biasing member is preferably coupled to each finger tracking element independently of the other finger tracking elements. Furthermore, the biasing member is preferably adjustable between a plurality of different resistance settings, each corresponding to a respective resistance force, so as to be arranged to provide a programmable resistance force acting to urge said at least one working element towards the starting position. The biasing member of each finger tracking element is preferably adjustable so as to vary the biasing force thereof independently of the biasing members of the other finger tracking elements.

When the working element is a plurality of finger tracking elements, in one embodiment the sensor element may comprise a plurality of finger sensors operatively coupled to the finger tracking elements respectively at the first side of the visual barrier, so that the indicator element comprises a plurality of finger indicators visible from a second side of the visual barrier which are operatively associated with the plurality of finger sensors respectively so as to be arranged to indicate displacement of the respective finger tracking elements independently of one another. Alternatively, the sensor element may comprise a single finger sensor operatively coupled to the plurality of finger tracking elements respectively at the first side of the visual barrier, so that the indicator element comprises a single finger indicator visible from a second side of the visual barrier which is operatively associated with the single finger sensor so as to be arranged to indicate displacement of any one of the finger tracking elements.

Preferably, said at least one working element further comprises a thumb tracking element arranged to be coupled to a respective thumb of the user, the thumb tracking element being movable against the biasing element in an opposing direction relative to the finger tracking elements.

The sensor element of the feedback mechanism may include a first sensor associated with the thumb tracking element and at least one second sensor associated with one or more of the finger tracking elements. In this instance, the indicator element preferably includes a first indicator responsive to the first sensor and a second indicator responsive to the at least one second sensor.

In the illustrated embodiment, the biasing member comprises an elastic, resilient member which is deformable from the starting position upon application of a force by a user and which returns to the starting position upon release of the force by the user. More particularly, the biasing member may be an elongate member which undergoes bending as said at least one working element is displaced from the starting position to the deflected position.

Preferably the indicator element of the feedback mechanism is dependent upon an amount movement of said at least one working element such that a magnitude of the movement of said at least one working element is indicated to the user.

In some embodiments, the at least one working element includes a socket having a central socket axis adapted to receive a finger tip of the user therein in which the working element is supported for movement in a working direction between the starting position and the deflected position, the socket being angularly adjustable through a range of angular positions about an adjustment axis that is oriented transversely to both the central socket axis and said working direction respectively.

The socket of said at least one working element may include a locking element enabling the socket to be fixed at a selected one of the angular positions throughout movement of the working element between the starting position and the deflected position. The socket of said at least one working element can also be supported to be freely pivotable between the different angular positions throughout movement of the working element between the starting position and the deflected position.

BRIEF DESCRIPTION OF THE DRAWINGS

Various embodiments of the invention will now be described in conjunction with the accompanying drawings in which.

In the drawings like characters of reference indicate corresponding parts in the different figures.

DETAILED DESCRIPTION

Figure 1:
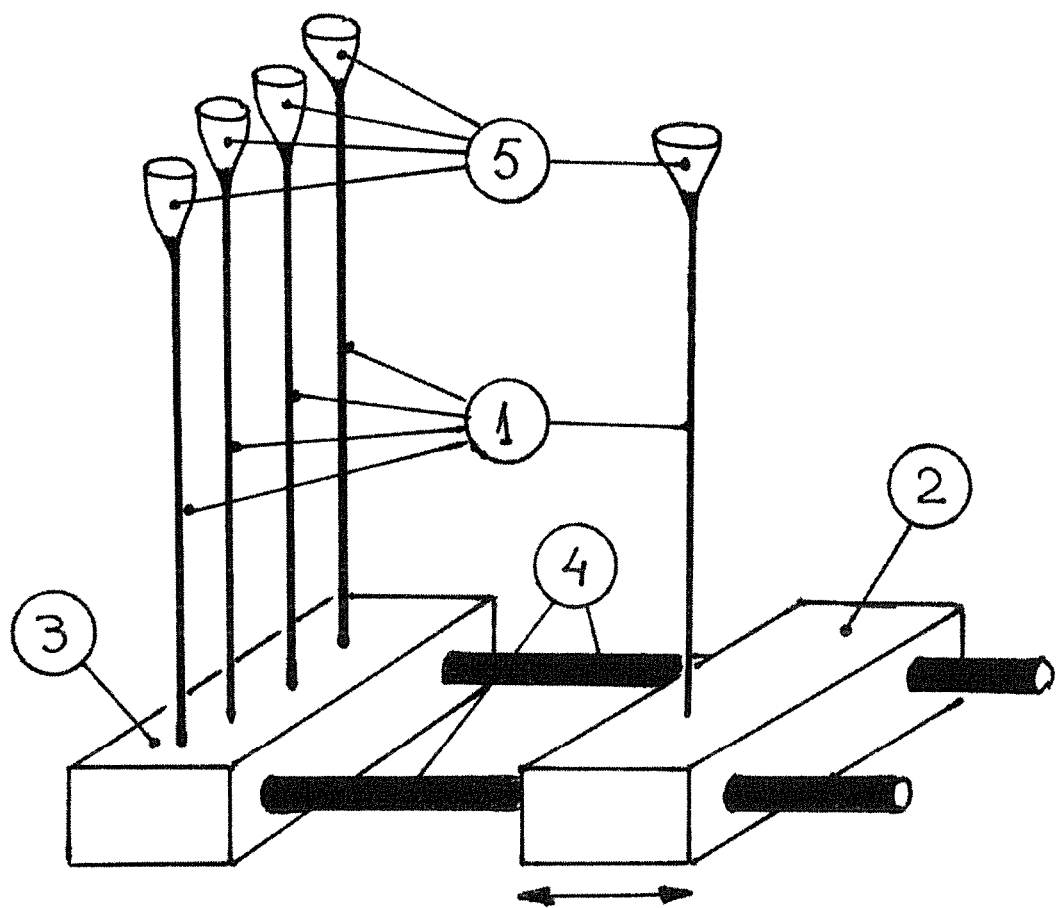
FIG. 1 is a schematic perspective view of the main components of the rehabilitation feedback system according to a first embodiment in which the components of the feedback mechanism and the visual barrier have been removed for illustrative purposes.
Figure 2:
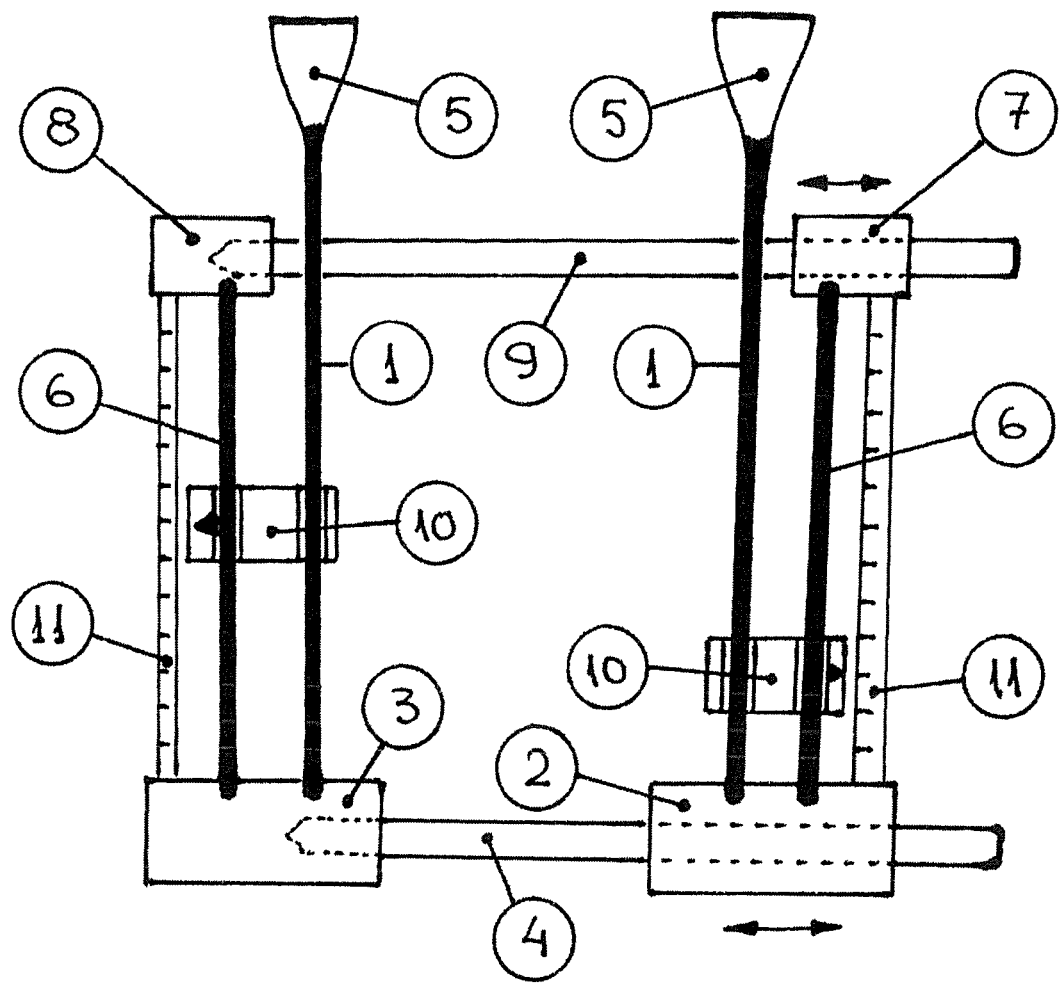
FIG. 2 is a schematic side view of the rehabilitation feedback system according to the first embodiment, illustrating the force adjustment and setting display.
Figure 3:
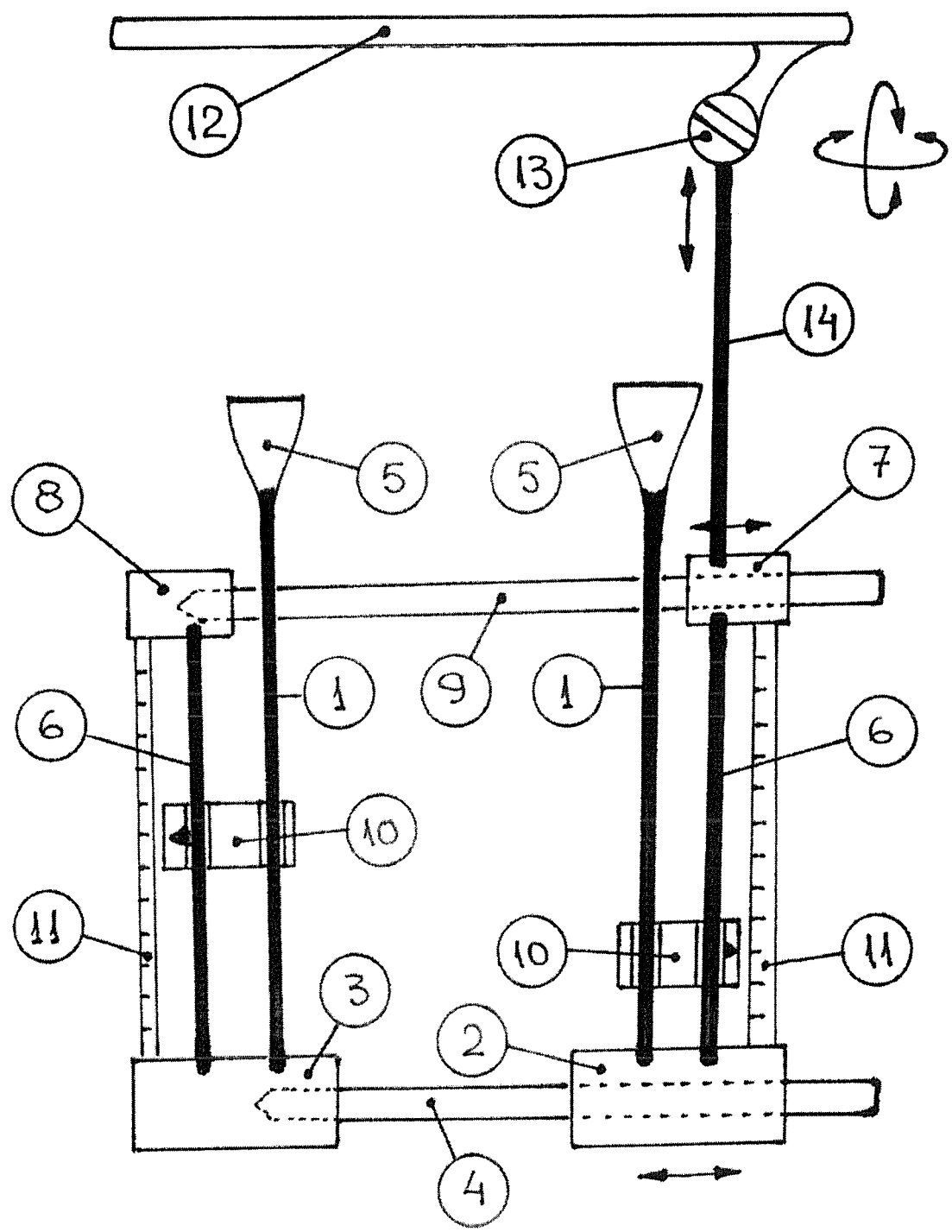
FIG. 3 is a schematic side view of the rehabilitation feedback system according to the first embodiment, illustrating the visual barrier for obscuring the hand of the user undergoing rehabilitation.

Referring to the accompanying figures, there is illustrated a preferred embodiment of a rehabilitation feedback system which provides a device that attaches to the extremities (distal phalanges) of each of the five fingers of either left or right hand, provides adjustable spacing to accommodate various hand sizes, offers individually adjustable and arbitrarily programmable resistance and range of motion for each finger, and prevents the user from seeing their hand while using the device. Performance feedback is provided indirectly, via a customizable graphical interface.

In each of the illustrated embodiments, the system includes five vertical elastic rods (1) installed on two base blocks—one rod on the thumb base block (2) and four rods on the fingers base block (3). The thumb base block (2) and the fingers base block (3) can slide along a common base slider system (4), to accommodate various hand sizes. Each rod is fitted at the upper (free) end with a finger cup (5) made of a flexible, non-slip material, deep enough to receive the corresponding finger's distal phalanges. The diameter of the finger cups is chosen—on a per-user basis—from a set of common sizes such that the finger tips are held tight but not uncomfortably squeezed during operation. The user inserts the fingers of the hand being trained into these cups, and attempts to bring them together in the center, simulating a grip movement involving the thumb and one (pinch grip), two (tripod grip), three (quad grip) or all four (ball grip) fingers. The elasticity of the rods is chosen so they can fully extend a relaxed hand of a healthy individual without creating a discomfort for the user.

Parallel with the elastic rods, and on the side opposite to the direction in which the elastic rods flex when gripped, there is one rigid rod (6) for each elastic rod (1). The thumb rigid rod is attached to the thumb base block (2) and the thumb top block (7). Each of the four finger rigid rods is attached the finger base block (3) and a common finger top block (8). The thumb top block (7) and the fingers top block (8) are connected by, can slide along and be locked onto a top slider system (9), to accommodate various hand sizes.

Between each elastic rod and its corresponding rigid rod there is a resistance setting slider (10) that can be moved along the rod pair, and locked into any location between the top and base blocks. The position of the resistance setting slider along the elastic rod determines the free length of the elastic rod—a lower position allows for a longer section of the elastic rod to flex (thus giving a lower resistance to grip) while a higher position reduces the free length of the elastic rod (thus giving a higher resistance to grip) for any of the five fingers independently. When placed at the top of the elastic rod (right next to the finger cup), the resistance setting slider blocks any movement of the corresponding finger. A force calibration scale (11) links the position of the force setting slider to actual force at the finger cup level (for example: 1 to 50N), or to an arbitrary resistance scale (for example: 1 to 10).

This possible embodiment of the invention hides the user's hand by means of an adjustable flat panel (12) attached to a swivel joint (13) with friction. The panel can be rotated about two horizontal axes, as well as raised or lowered along the telescopic leg (14) such that it obscures the hand from the user's direct view while leaving enough space between the panel and the finger cups to allow for comfortable insertion of fingers into the finger cups and exercise of the hand.

In this possible embodiment of the invention, movement feedback is given to the user via a pair of U-frames (15) attached to the base blocks. These U-frames are elastic, and installed in such a way that they stay in contact with the elastic rods and bend along with them during exercise, without adding significant resistance to the grip movement. Each of the two U-frames is attached via a joint (16) to a mobile feedback rod (17) that extends towards the fingers side so that its free end is visible to the user. A fixed feedback rod (18) is solidly attached to the fingers top block and extends towards the finger side such that its free end is visible to the user. A system of pointers (19) are attached to the mobile feedback rods via joints (20) and slide along the fixed feedback rods so that the user perceives the fingers movements as movements of the pointers relative to each other. One fixed pointer (21) provides a reference point for the movement of thumb and fingers relative to the grip target location.

Due to its small size and weight, the device can be positioned in various orientations with reference to the user's hand—through an optional support system such as a tripod—to accommodate for any possible deformity or pathological orientation or resting configuration of the affected hand.

In the illustrated embodiment, the base blocks (2, 3) and the rods (4) collectively form a base frame. The finger cups (5) which are also described herein as working element for the fingers and thumb, define finger tracking elements and a thumb tracking element for tracking movement of the respective fingers and thumb relative to the base frame. The flexible elastic rods (1) define a biasing member which support the working elements to be movable relative to the base frame from a starting position to a deflected position together with the movement of the fingers of the user while providing a resistance force acting to urge said at least one working element towards the starting position. The panel (12) acts as a visual barrier between the fingers coupled to the working elements at a first side of the visual barrier and direct visual sight by the user at a second side of the visual barrier. A feedback mechanism includes first and second sensor elements (15) at the first side of the visual barrier for operative connection to the working elements (5) on the rods (1) so as to be arranged to detect any degree or amount of movement of the working element away from the starting position. The feedback mechanism further includes first and second indicator elements (19) operatively connected to the first and second sensor elements (15) respectively. The first and second indicator elements (19) are located at the second side of the visual barrier so as to be arranged to indicate to the user an amount of displacement of the finger and thumb tracking elements respectively in response to detection by the sensor elements that the finger and thumb tracking elements have moved away from the starting position respectively.

Another possible embodiment of this invention uses electromechanical sensors to measure the displacement for each finger and the thumb individually. In this embodiment, a frame-side arm (22) and a rod-side arm (23) are connected at one end by a spherical joint (24). The frame-side arm (22) is attached to the common finger top block (8) via a spherical joint (25). The rod-side arm (23) is connected to the rod (1) via a spherical joint (26) built on a sleeve (27) permanently attached to the rod (1). The frame-side arm (22) embeds a magnetic field sensor (28). At the same distance from the spherical joint (24) but along the rod-side arm, a magnet (29) is embedded, such that the magnetic field sensor (28) and the magnet (29) are facing each other, while the spacing between them is proportional to the displacement of the finger cup (5) away from the resting position. The spherical joints allow for rod (5) movements both towards the facing thumb rod (1) or sideways, without restricting finger movements in any ways other than the resistance adjusted through the resistance setting slider (10). Compared to the mechanical feedback system, this embodiment has the advantage of measuring displacement for each finger independently, thus allowing for more precise assessment of the user performance and finer grained feedback.

In yet another embodiment of this invention, a modified version of the finger cups (30) allows them to be oriented at various angles with reference to the direction of the rod (1). In this embodiment, the orientable finger cup (30) is attached to the rod (1) by means of a rod cap (31) via a joint (32) that allows the cup to rotate around the joint axis such that the cup can change its orientation with reference to the rod (1) axial direction. The joint (32) can be locked in any particular position (thus forcing the user to exercise a particular grasp), or let loose such that the cup (30) can follow the fingertip orientation, giving the user more freedom of movement, as required by the specific exercise being undertaken.

Other alternative embodiments of this invention can use other mechanical arrangements or actuators to generate resistance and control ranges of motion; they can also use displacement and force sensors to read forces and movements, and computerized graphic user interfaces for user feedback. Audio feedback (sounds or spoken messages) can also be provided. Other embodiments can include processing power to provide additional features, self-learning and artificial intelligence capabilities for the device, as well as communication interfaces to allow for remote monitoring and control by a healthcare professional via a data link (phone line, radio communications, the Internet), or to allow team exercising and interactions among geographically-separated users.

One Example of the Use:

A left-handed stroke survivor has her left side of the body affected by the stroke. Her left hand has very limited mobility but she retained tactile sensations in her fingertips. Her cognitive performance may or may not be affected by the stroke. She would like to be able to pick up small objects and hold a spoon or fork using her left thumb, pointer finger and middle finger.

She can use the device to specifically retrain sensorimotor functionality of the three fingers for this particular use. She will use her healthy right hand to set up the device. A typical training session consists of the following steps: (i) set resistance for the thumb, pointer and middle fingers to 5; (ii) set resistance for the ring and small finger to 10 (to block them, thus preventing them from contributing to the indirect feedback); (iii) insert the fingers of her left hand into the finger cups; (iv) adjust the top and bottom block sliders to match her hand size; (v) adjust the position of the barrier panel so that she can not see her left hand during exercise; (vi) place the fixed pointer halfway between the mobile pointers; (vii) start exercising; during each grip, she would focus on bringing both mobile pointers in contact with the fixed pointer at the same time (This condition translates into a symmetrical movement of the fingers—thumb travel is equal to index and middle finger travel); (viii) as the precision of the grip increases and the execution time decreases, she would reduce the resistance setting for the fingers involved while keeping it at the same level for all three, and continue exercising (Lower resistance requires a higher level of control to avoid overshooting the target movement); (ix) once she is happy about the overall grip performance (speed, precision), she can set the resistance level for each finger differently, to train individual finger motion control; (x) as the movement precision increases, she can place the fixed pointer closer to one or the other mobile pointer (which translates into different travel distances for thumb vs fingers) while focusing on both mobile pointers coming in contact with the fixed pointer at the same time; (xi) she should stop exercising once fatigue appears, and resume training after adequate rest, always starting with a slightly easier task than the last one successfully performed during the previous training session.

As described herein, the feedback system shown in the figures includes a base frame comprised mainly of the lower thumb block 2, the lower finger block 3, the upper thumb block 7, and the upper finger block 8 which are supported in fixed relation to one another at a plurality of different spacings in the longitudinal direction. Each of the blocks extends generally in a lateral direction such that the two lower blocks are spaced apart in a longitudinal direction by the crossbars 4 interconnected between the lower blocks. As described above, one or both of the lower blocks may be slidable along the crossbars to adjust the longitudinal spacing between the lower blocks. Similarly, the upper blocks are connected by upper crossbars 9 which are oriented to extend in the longitudinal direction between the upper blocks 7 and 8 at laterally spaced apart positions. Again, one or both of the upper blocks 7 or 8 are slidable relative to the upper crossbars 9 when adjusting the longitudinal spacing between the blocks to accommodate different user hand sizes.

At the finger side of the frame, four resilient rods 1 extend up from the lower block so as to be evenly spaced apart within a single row oriented in the lateral direction perpendicular to the longitudinal direction of adjustment of the frame. At the starting position, the rods can be located in close proximity to an inner surface of the corresponding upper block 8 such that finger cups 5 which define finger tracking elements are supported at the top end of the rods within a generally common horizontal plane and such that the cups are movable in a working direction oriented generally in the longitudinal direction towards the opposing upper block 7 as the elements are displaced from the starting position to the deflected position thereof.

Figure 4:
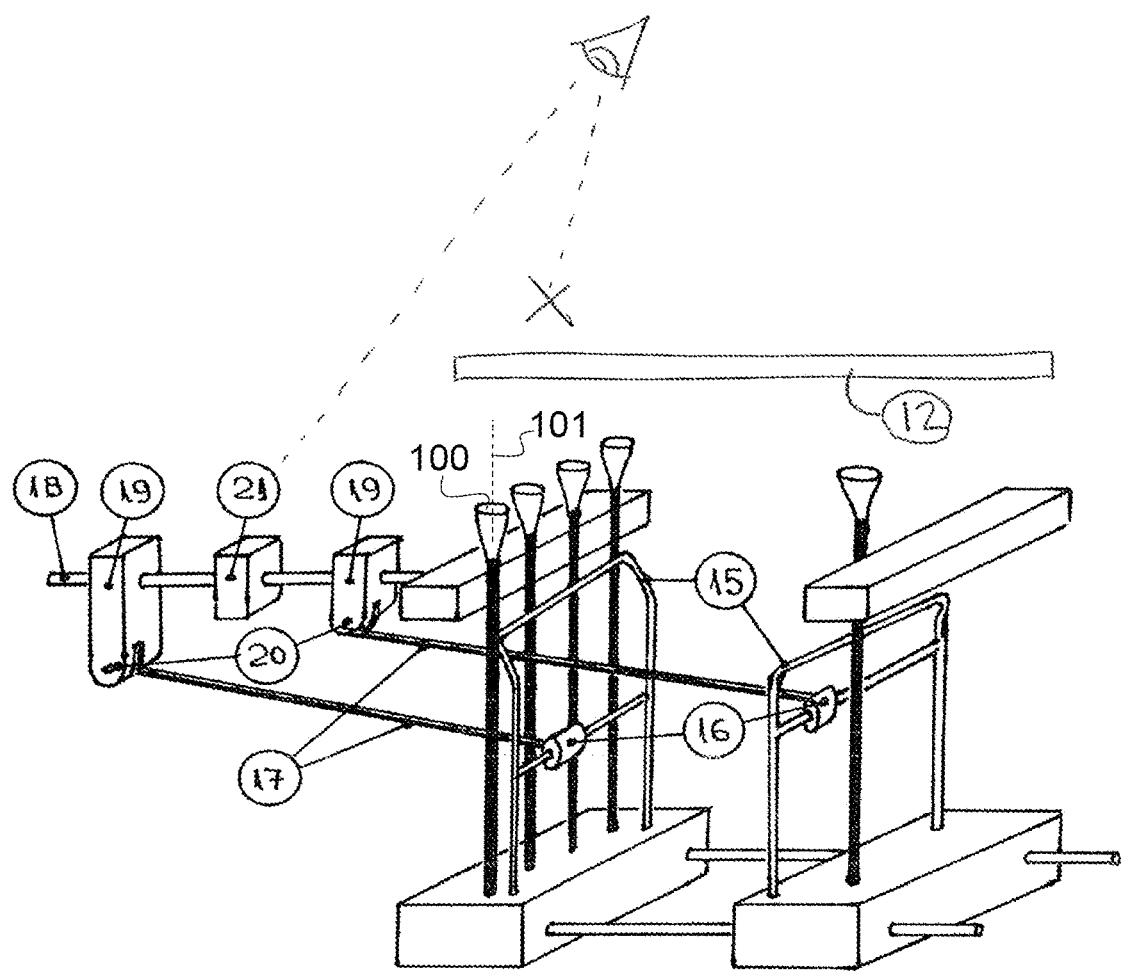
FIG. 4 is a schematic perspective view of the rehabilitation feedback system according to the first embodiment, illustrating the indirect feedback mechanism.

Referring, for example, to FIG. 4, each of the finger cups comprises a socket 100 having an open top end which surrounds a central socket axis 101 so as to be suitable for receiving a respective finger tip of the user therein so that the finger tracking element can be coupled to the finger of the user and movable together with the finger of the user from the starting position to the deflected position. According to the first embodiment, the finger cups are fixed in orientation relative to the rods upon which they are supported such that the socket axis is perpendicular both to the lateral direction and the longitudinal direction corresponding to the working direction of movement from the starting position towards the deflected position thereof.

Figure 6:
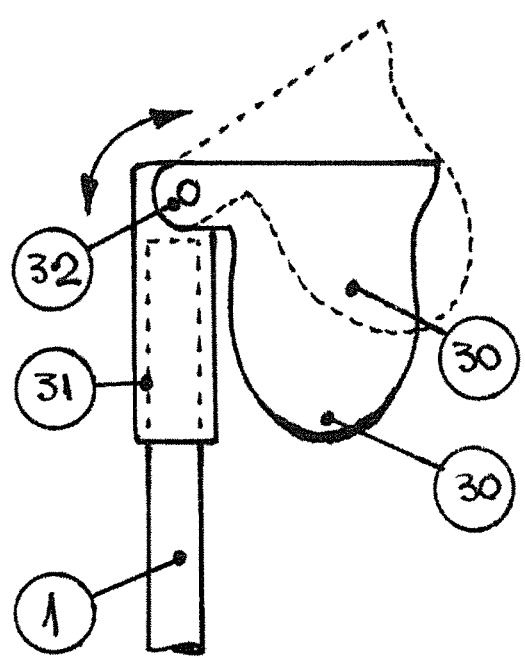
FIGS. 6(a), 6(b), 6(c) and 6(d) are schematic representations of an alternative arrangement of the working elements for use with the feedback system according to either one of the embodiments of FIG. 1 or 5, in which the working elements each include an orientable finger cup which can be adjusted between different angular orientations relative to the working element upon which it is supported.
Figure 6:
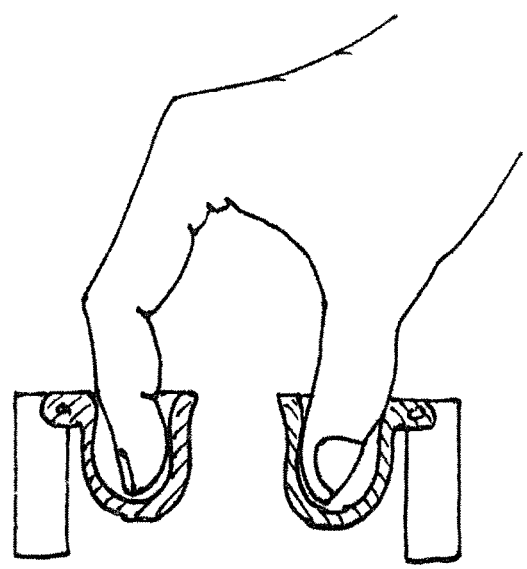
Figure 6:
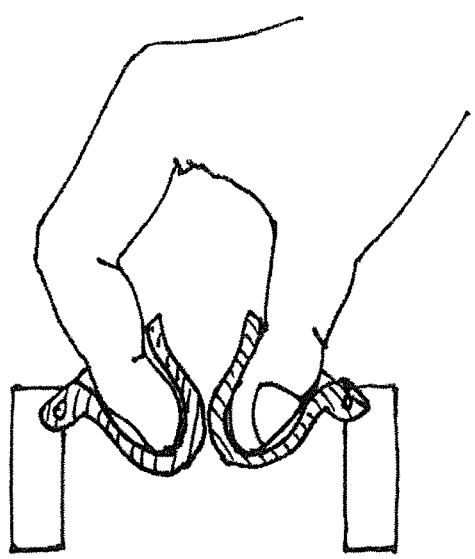
Figure 6:
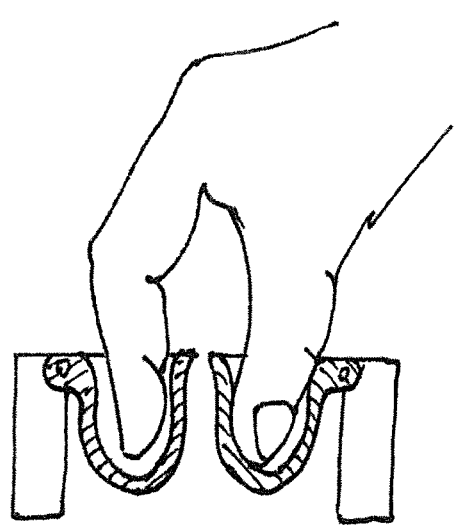

Alternatively, according to the embodiments of FIGS. 6(a) through 6(d), the finger cups may be supported such that the cups are angularly adjustable about an adjustment axis (for example, passing through joint 32 in FIG. 6(a)) which is oriented in the lateral direction such that the adjustment axis is perpendicular to the working direction of movement as well as being perpendicular to the longitudinal direction of the base frame and perpendicular to the socket axis. In some instances, it may be desirable to provide a locking element (such as, for example, a set screw) which fixes the orientation of the finger cup relative to the rod at a selected angular orientation throughout movement of the finger cup between the starting position and the deflected position thereof; however, in other instances it may be desirable to support the finger cup such that it remains freely pivotal to vary in angular orientation throughout the movement of the finger cup between the starting position and the deflected position thereof.

At the longitudinally opposed end of the frame from the row of finger tracking elements, the lower block 2 at the thumb side of the frame supports a single rod 1 with a single finger cup 5 at the top end thereof which is substantially identical in configuration to the finger cups supported on the rods for the finger tracking elements. The single rod and 1 at the thumb side defines a thumb tracking element which is initially positioned and un-flexed state in close proximity to an inner surface of the upper block 7. The thumb tracking element is movable in a working direction which is opposite to the working direction of the finger tracking elements such that the finger cup of the thumb tracking element is movable generally in the longitudinal direction of the frame from the starting position to the deflected position thereof towards the opposing finger tracking elements. In the initial unflexed position of the rod 1 of the thumb tracking element, the finger cup 5 of the thumb tracking element lies in a substantially common horizontal plane with the finger cups of the finger tracking elements. In use, when the user places there thumb in the thumb tracking element and their fingers in the respective cups of the finger tracking elements and exerts a gripping motion, each of the thumb tracking element and the finger tracking elements are movable towards one another and relative to the frame.

The rods 1 in the instance of both the finger tracking elements and the thumb tracking elements are arranged to extend generally linearly in an unflexed position corresponding to the starting position of the working elements. As the elements are displaced towards one another, the respective rods 1 undergo bending deflection so as to be deformed from the starting position upon application of a forced by a user so that the resistance force urges the resilient member to return to the starting position upon release of the forced by the user. The resistive force as a result of the bending impose on the rod can be adjusted using the blocks 10 described above which are slidable along respective fixed rods 6. Each fixed rod 6 is rigid and substantially non-flexible, while the mounted parallel to a respective one of the rods 1 of the working elements. Each slider block is supported to be longitudinally slidable along the respective fixed rod 6 and provides an aperture therein through which the corresponding flexible rod 1 is slidably received. A suitable locking element such as a set screw can retain the block 10 at a selected elevation along the respective pair of rods 1 and 6 upon which the block is supported. Each selected elevation among a range of elevations of the block 10 corresponds to a different resistive force being applied by the flexible rod 1 against the movement of the corresponding finger cup 5 a from the starting position towards the deflected position thereof. Variation in the elevation of the block 10 effectively shortens the uncoupled length of the rod 1 between the block 10 and the finger cup 5 in which the uncoupled length of the rod is the remaining portion of the rod that is free to undergo bending. A shorter uncoupled length of the rod is required to undergo a greater degree of bending for the same distance of movement of the associated finger cup 5 in the longitudinal working direction from the starting position towards the deflected position thereof which corresponds to a greater resistive force to the movement. As each rod 1 is provided with its own block numeral 10 for adjusting the force thereof, the resistive force among all working elements can be adjusted independently of one another.

Figure 5:
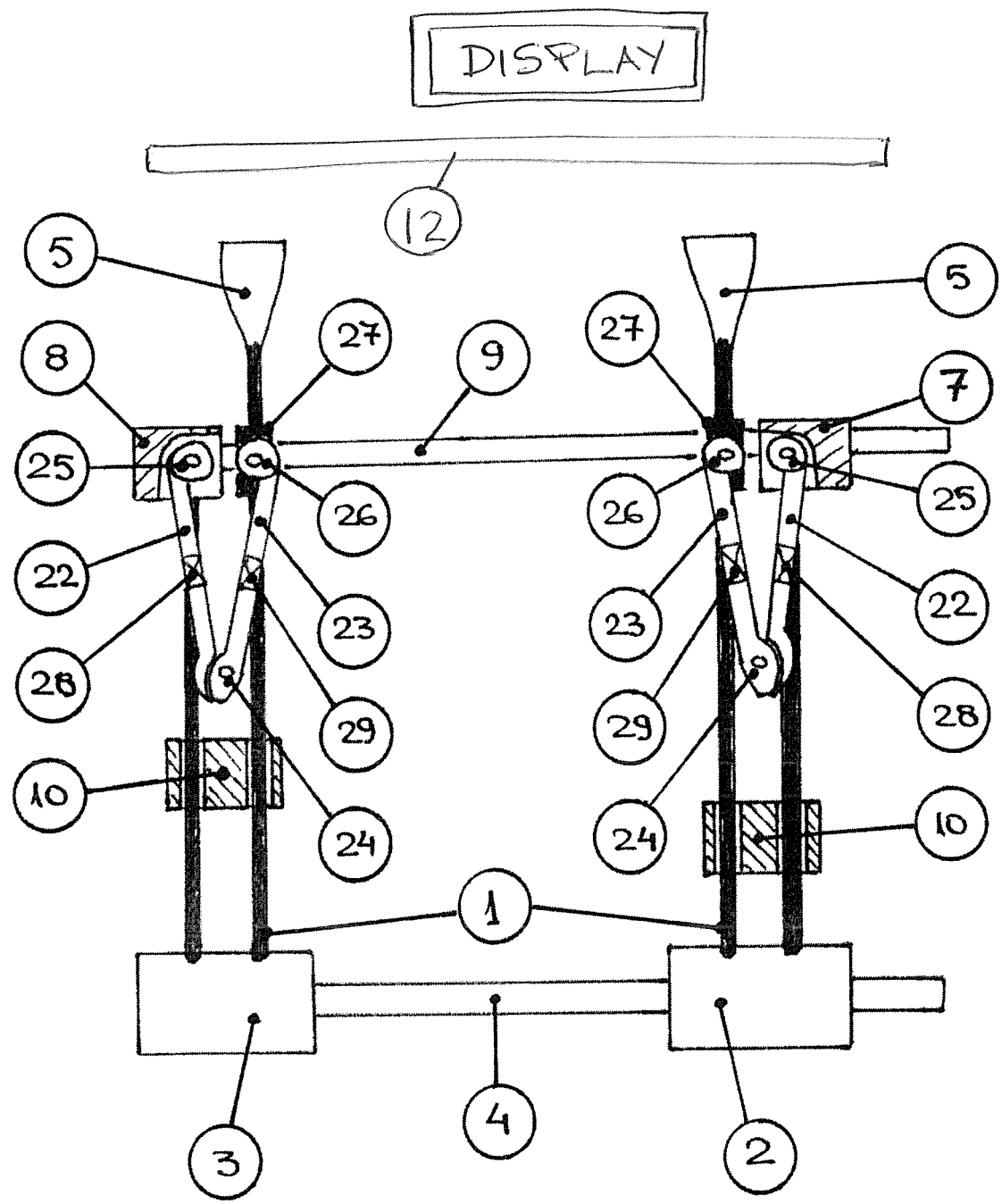
FIG. 5 is a schematic side view of the rehabilitation feedback system according to a second embodiment, illustrating a variation of the indirect feedback mechanism using electromechanical displacement sensors which communicate with a display monitor on the opposing side of the visual barrier.

The feedback mechanism comprised of one or more sensing elements and one or more indicator elements may take the form of a mechanical system according to the embodiment of FIGS. 1 through 4 or take the form of an electromechanical system
according to the embodiment of FIG. 5. In the first embodiment, each flexible frame 15 defines an input linkage bar spanning in the lateral direction along the inner side of the respective row of finger tracking elements or the thumb tracking element. Accordingly if any one of the finger tracking elements is displaced inwardly towards the deflected position thereof, the input linkage bar of the frame 15 will be displaced inwardly towards the opposing end of the base frame. Likewise, if the thumb tracking element is displaced inwardly towards the deflected position thereof, the corresponding input linkage bar of the frame 15 at the thumb side will be displaced inwardly towards the opposing end of the base frame. The frames 15 define sensor elements for sensing the movement of the working elements at the first side of the visual barrier 12 so as to be obstructed from view by the user.

An indicator bar 18 is supported to extend in the longitudinal direction at a location offset from the visual barrier so as to be visible to the user at the second side of the visual barrier 12. A central marker 21 is mounted at a central location on the bar 18. The central marker 21 can be adjusted in position along the bar when calibrating the indicator relative to the size of the hand of the user, but once calibrated is fixed in position relative to the bar 18, for example using a set screw. In addition, finger and thumb indicator members 19 are also mounted on the indicator bar so as to be slidable along the bar at opposing sides of the central marker 21. Each indicator member 19 is coupled to a respective one of the frames 15 by a suitable linkage member 17 such that each of the indicator members 19 is slidable along the indicator bar 18 in the longitudinal direction of the base frame in direct proportion to the movement of the sensor frames 15 in the longitudinal direction of the base frame. Other linkages may couple the indicator members 19 relative to the sensor frames 15 such that there is a relationship between the movement even if the movement is not a direct linear proportion. In either instance, it is desirable for the indicator member movement to indicate both that a movement of the working elements has occurred, and a magnitude of that movement.

In the instance of electromechanical sensing elements according to FIG. 5, an individual sensing element may be coupled to each one of the working elements using a suitable electronic sensor capable of generating an output signal representative of the amount of movement of the corresponding working element with which it is associated. In this instance, a suitable display monitor can be located at the second side of the visual barrier 12 opposite from the working elements and sensing elements at the first side of the barrier, and the display monitor can be in communication with the sensor elements for displaying a graphical representation of the output signal associated with each sensor. Accordingly the graphical display can graphically represent an independent indicator element associated with each of the sensor elements which indicates when a movement of that working element has occurred, in addition to displaying a magnitude of that movement.

Since various modifications be made in my invention as herein above described, and many apparently widely different embodiments of same made, it is intended that all matter contained in the accompanying specification shall be interpreted as illustrative only and not in a limiting sense.

The invention claimed is:

1. A rehabilitation feedback system for use during rehabilitation of control by a user of one or more body appendages of the user, the system comprising:
   a base frame;
   at least one working element supported on the base frame so as to be movable relative to the base frame from a starting position to a deflected position, said at least one working element being adapted to be coupled to a respective one of the one or more body appendages of the user for movement with the body appendage relative to the base frame;
   a biasing member operatively connected between the base frame and said at least one working element so as to provide a resistance force acting to urge said at least one working element towards the starting position;
   a visual barrier adapted to hide the one or more body appendages of the user at a first side of the visual barrier from direct visual sight by the user at a second side of the visual barrier;
   a sensor element at the first side of the visual barrier so as to be arranged to detect movement of said at least one working element away from the starting position; and
   an indicator element which is detectable by the user from a second side of the visual barrier and which is arranged to indicate to the user a displacement of said at least one working element in response to detection by the sensor element that said at least one working element has moved away from the starting position.

2. The system according to claim 1 wherein said at least one working element is arranged to be coupled to a finger of the user.

3. The system according to claim 1 wherein the biasing member is adjustable between a plurality of different resistance settings, each corresponding to a respective resistance force, so as to be arranged to provide a programmable resistance force acting to urge said at least one working element towards the starting position.

4. The system according to claim 1 wherein said at least one working element comprises a plurality of finger tracking elements arranged to be coupled to respective fingers of the user for tracking a gripping motion of the fingers of the user.

5. The system according to claim 4 wherein the biasing member is coupled to each finger tracking element independently of the other finger tracking elements.

6. The system according to claim 5 wherein the biasing member of each finger tracking element is adjustable so as to vary the biasing force thereof independently of the biasing members of the other finger tracking elements.

7. The system according to claim 4 wherein the sensor element comprises a plurality of finger sensors operatively coupled to the finger tracking elements respectively at the first side of the visual barrier, and the indicator element comprises a plurality of finger indicators visible from a second side of the visual barrier which are operatively associated with the plurality of finger sensors respectively so as to be arranged to indicate displacement of the respective finger tracking elements independently of one another.

8. The system according to claim 4 wherein the sensor element comprises a single finger sensor operatively coupled to the plurality of finger tracking elements respectively at the first side of the visual barrier, and the indicator element comprises a single finger indicator visible from a second side of the visual barrier which is operatively associated with the single finger sensor so as to be arranged to indicate displacement of any one of the finger tracking elements.

9. The system according to claim 4 wherein said at least one working element further comprises a thumb tracking element arranged to be coupled to a respective thumb of the user, the thumb tracking element being movable against the biasing element in an opposing direction relative to the finger tracking elements.

10. The system according to claim 9 wherein the sensor element includes a first sensor associated with the thumb tracking element and at least one second sensor associated with one or more of the finger tracking elements, and wherein the indicator element includes a first indicator responsive to the first sensor and a second indicator responsive to the at least one second sensor.

11. The system according to claim 1 wherein the biasing member comprises a resilient member which is deformable from the starting position upon application of a force by a user and which returns to the starting position upon release of the force by the user.

12. The system according to claim 11 wherein the resilient member is an elongate member which undergoes bending as said at least one working element is displaced from the starting position to the deflected position.

13. The system according to claim 1 wherein the indicator element is dependent upon an amount of movement of said at least one working element such that a magnitude of the movement of said at least one working element is indicated to the user.

14. The system according to claim 1 wherein said at least one working element includes a socket having a central socket axis adapted to receive a finger tip of the user therein in which the working element is supported for movement in a working direction between the starting position and the deflected position, the socket being angularly adjustable through a range of angular positions about an adjustment axis that is oriented transversely to both the central socket axis and the working direction respectively.

15. The system according to claim 14 wherein the socket of said at least one working element including a locking element enabling the socket to be fixed at a selected one of the angular positions.

16. The system according to claim 14 wherein the socket of said at least one working element is supported to be freely pivotable between the different angular positions.

17. A method of providing movement feedback to a user undergoing rehabilitation of control by the user of a body appendage of the user, the method comprising:
providing a rehabilitation feedback system comprising (i) a base frame, (ii) at least one working element supported on the base frame so as to be movable relative to the base frame from a starting position to a deflected position, (iii) a biasing member operatively connected between the base frame and said at least one working element so as to provide a resistance force acting to urge said at least one working element towards the starting position, (iv) a sensor element arranged to detect movement of said at least one working element away from the starting position, and (v) an indicator element arranged to indicate to the user a displacement of said at least one working element in response to detection by the sensor element that said at least one working element has moved away from the starting position;
providing a visual barrier in proximity to the rehabilitation system such that said at least one working element is hidden at a first side of the visual barrier from direct visual sight by the user at a second side of the visual barrier;
locating the indicator element so as to be detectable by a user from the second side of the visual barrier; and
operating the feedback system such that any movement relative to the base frame of a body appendage of the user that is coupled to said at least one working element at the first side of the visual barrier is indicated to the user in a manner that is detectable by the user from the second side of the visual barrier.

18. The method according to claim 17 including coupling said at least one working element to a finger of the user so as to provide feedback to the user undergoing rehabilitation of control by the user of the finger of the user.

19. The method according to claim 17 including adjusting the biasing member between a plurality of different resistance settings, each corresponding to a respective resistance force acting to urge said at least one working element towards the starting position.

20. The method according to claim 17 wherein said at least one working element comprises a plurality of finger tracking elements, the method including coupling the finger tracking elements to respective fingers of the user so as to provide feedback to the user relating to a gripping motion of the fingers of the user.

* * * * *